(12) United States Patent
Wang et al.

(10) Patent No.: US 11,839,607 B2
(45) Date of Patent: Dec. 12, 2023

(54) MEMANTINE PAROXETINE COCRYSTAL SALT AND ITS PREPARATION METHOD, PHARMACEUTICAL COMPOSITION AND APPLICATION

(71) Applicant: HEFEI KEDA BIO-TECHNOLOGY CO. LTD, Hefei (CN)

(72) Inventors: Ke Wang, Hefei (CN); Qianliu Cheng, Hefei (CN); Zonggui Wang, Hefei (CN); Yan Geng, Hefei (CN); Xun Zhao, Suzhou (CN)

(73) Assignee: HEFEI KEDA BIO-TECHNOLOGY CO. LTD, Hefei (CN)

( * ) Notice: Subject to any disclaimer, the term of this patent is extended or adjusted under 35 U.S.C. 154(b) by 631 days.

(21) Appl. No.: 16/978,202

(22) PCT Filed: Feb. 22, 2019

(86) PCT No.: PCT/CN2019/075891
§ 371 (c)(1),
(2) Date: Sep. 4, 2020

(87) PCT Pub. No.: WO2019/170009
PCT Pub. Date: Sep. 12, 2019

(65) Prior Publication Data
US 2021/0038590 A1 Feb. 11, 2021

(30) Foreign Application Priority Data
Mar. 8, 2018 (CN) .......................... 201810190483.4

(51) Int. Cl.
| | |
|---|---|
| *A61K 31/4525* | (2006.01) |
| *A61K 31/13* | (2006.01) |
| *A61K 31/265* | (2006.01) |
| *A61K 31/445* | (2006.01) |
| *A61K 31/55* | (2006.01) |
| *C07C 211/38* | (2006.01) |
| *C07D 405/12* | (2006.01) |

(52) U.S. Cl.
CPC .......... *A61K 31/4525* (2013.01); *A61K 31/13* (2013.01); *A61K 31/265* (2013.01); *A61K 31/445* (2013.01); *A61K 31/55* (2013.01); *C07C 211/38* (2013.01); *C07D 405/12* (2013.01); *C07B 2200/13* (2013.01)

(58) Field of Classification Search
CPC ............ C07B 2200/13; C07C 2603/74; C07C 211/38; C07D 405/12
See application file for complete search history.

(56) References Cited

FOREIGN PATENT DOCUMENTS

| WO | WO-9940084 A1 * | 8/1999 | ........... C07D 405/12 |
| WO | 2005079756 A2 | 9/2005 | |
| WO | WO-2009109401 A1 * | 9/2009 | ........... C07C 211/38 |

OTHER PUBLICATIONS

Polymorphs, Salts, and Cocrystals: What's in a Name? Cryst. Growth Des. 2012, 12, 2147-2152 (Year: 2012).*
Polymorphism in cocrystals: a review and assessment of its significance CrystEngComm, 2014, 16, 3451-3465 (Year: 2014).*
Pharmaceutical Cocrystals: Regulatory and Strategic Aspects, Design and Development Advanced Pharmaceutical Bulletin, 2016, 6(4), 479-494 (Year: 2016).*
N. Duggirala et al., 52 Chem. Commun., 640-655 (2016). (Year: 2016).*

* cited by examiner

*Primary Examiner* — Brandon J Fetterolf
*Assistant Examiner* — Frank S. Hou
(74) *Attorney, Agent, or Firm* — Bayramoglu Law Offices LLC

(57) ABSTRACT

A memantine paroxetine cocrystal salt and its preparation method, pharmaceutical composition and application thereof are provided. The cocrystal salt of the invention is memantine paroxetine sulfate hydrate. Its mechanism of action is 5-HT inhibitor and NMDA receptor antagonist. It is a multi-target drug. The preliminary pharmacokinetic experiments showed that the main pharmacokinetic parameters of cocrystal salt and memantine, such as $T_{1/2}$, $T_{max}$, $C_{max}$ and $AUC_{(0-\infty)}$, were significantly different. The results also showed that cocrystal salt could improve drug absorption, blood drug concentration, bioavailability and curative effect. This provides a material basis for reducing dosage and adverse drug reactions. In addition to that the cocrystal salt of this invention can be used as a multi-target drug, it can also combine with other drugs of different action mechanisms to form compound preparations or be used in combination, so as to obtain unexpected clinical efficacy.

10 Claims, 5 Drawing Sheets

MEMANTINE PAROXETINE COCRYSTAL SALT AND ITS PREPARATION METHOD, PHARMACEUTICAL COMPOSITION AND APPLICATION

CROSS REFERENCE TO THE RELATED APPLICATIONS

This application is the national phase entry of International Application No. PCT/CN2019/075891, filed on Feb. 22, 2019, which is based upon and claims priority to Chinese Patent Application No. 201810190483.4, filed on Mar. 8, 2018, the entire contents of which are incorporated herein by reference.

TECHNICAL FIELD

The invention relates to the field of drug synthesis technology, and more specifically to a memantine paroxetine cocrystal salt and its preparation method, pharmaceutical composition and application.

BACKGROUND

Alzheimer's disease (AD) is also called senile dementia. This is a degenerative disease of the central nervous system that is characterized by impaired daily living, behavioral abnormalities and cognitive dysfunctions. Patients with neurodegenerative disease often have symptoms of depression. According to incomplete statistics, about 25%-40% of people with Alzheimer's disease may suffer from depression. Depression and AD contribute to the development of the disease. Chronic stress is the primary cause of depression and AD. In 2011, Kobayashi et al. proposed the concept of "depression-dementia intermediate state", believing that patients in the "depression-dementia intermediate state" can prevent or delay the occurrence of AD if they receive timely and effective treatment. In 2002, the National Institute of Mental Health established criteria for diagnosing depression in people with Alzheimer's disease. Its specific requirements are: while the patients meet the AD diagnosis standard, they must have three or more symptoms of depression, such as depressive emotions, insomnia, loss of appetite, drop of psychomotor excitement, agitation, burnout, reduction of interest or pleasure in society and daily life, retreat from social life, self-denial, helplessness, Seneca, suicide, etc. The standard requires the patients' depression symptoms to last more than two weeks. It is enough to show that Alzheimer's disease and depression do have certain clinical characteristics of correlation.

Patients with Alzheimer's disease, depression or co-patients with both diseases are difficult and hot spots for the development of clinical drugs at present, which have not been satisfied by clinical treatment at present and are in urgent need of clinical development. Both diseases have become major public health problems in the world.

There are certain comorbidities between depression and AD. In recent years, clinical studies have shown that some antidepressants can be used to improve the symptoms of depression associated with AD and further improve the symptoms of dementia, mainly including SSRIs and natural antidepressants. At present, relevant studies have shown that antidepressants can improve and prevent Alzheimer's disease to a certain extent. In recent years, antidepressants are often used in clinical adjuvant treatment of Alzheimer's disease, and some results have been achieved.

The chemical name of memantine hydrochloride is 3, 5-Dimethyl-1-aminoadamantane hydrochloride, and 3,5-Dimethyltricyclo (3.3.1.1 (3,7) decan-1-aminehydrochloride). Its molecular formula is $C_{12}H_{21}N \cdot HCl$, a dementia drug developed by Merz Company in Germany. Its structural formula is as follows:

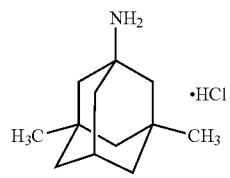

Memantine hydrochloride is a new, low-moderate affinity, voltage-dependent, non-competitive N-methyl-D-aspartic acid (NMDA) receptor antagonist. It can block NMDA receptor in a non-competitive way, reduce over-excitation of NMDA receptor caused by glutamate, prevent apoptosis and improve memory. It is a new generation of drugs to improve cognitive function. In February 2002, it was approved by CPMP to be used in the treatment of Alzheimer's disease from moderate to severe levels. In August of the same year, it was launched in Germany. On Oct. 17, 2003, it was approved by the US Food and Drug Administration (FDA) to be used in the treatment of Alzheimer's disease from moderate to severe levels. Further studies have shown that memantine hydrochloride is effective in patients with Alzheimer's disease from mild to moderate levels. The recommended dosage for the first week is 10 mg/d, and the maximum daily dose for an adult is 20 mg, with the molecular weight of 215.76 and the free alkali molecular weight of 179.3.

Paroxetine mesylate or paroxetine hydrochloride is used to treat various types of depression, including depression with anxiety and reactive depression. Its molecular formula is $C_{20}H_{24}FNO_6S$ or $C_{19}H_{21}ClFNO_3$, and its structural formula is as follows:

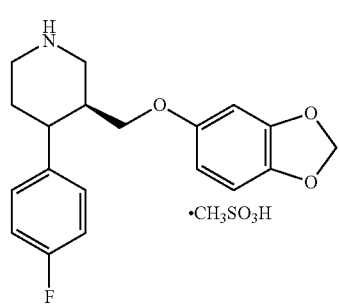

paroxetine mesylate

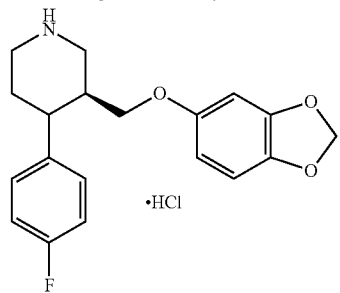

paroxetine hydrochloride

The recommended initial dose of paroxetine mesylate for the treatment of major depressive disorder is 20 mg/d and can be gradually increased to a maximum of 50 mg/d. In the treatment of panic disorder, the initial dose is 10 mg/d and can be increased to a maximum of 60 mg/d. In the treatment of OCD, the initial dose is 20 mg/d and can be gradually increased to a maximum of 60 mg/d. Its molecular weight is 425.47 and the molecular weight of free alkali is 329.37. When conjugated at a molar ratio of 1:1, memantine and paroxetine are used in pharmaceutical preparations in accordance with the dosage range of individual preparations.

Therefore, (NMDA) receptor antagonists and SSRI antidepressants can be used to prevent and treat Alzheimer's disease. As the pathogenesis of Alzheimer's disease is very complex and the etiology is not yet clear, it cannot be completely controlled by single therapy. The combination of drugs with different mechanisms of action may have good effects.

SUMMARY

The technical problem to be solved by the invention is how to obtain cocrystal drugs of memantine and paroxetine with better efficacy, higher bioavailability, lower dosage and less adverse reactions.

The invention has solved the above technical problems through the following technical solutions:

It is memantine paroxetine cocrystal salt. The molecular formula of the memantine paroxetine cocrystal salt is $C_{19}H_{20}FNO_3 \cdot C_{12}H_{21}N \cdot H_2SO_4 \cdot XH_2O$, where $0 \leq X \leq 5$, and the memantine molecule is bound to the paroxetine molecule by non-covalent bonds.

Further, X=3.

Further, the X-ray powder diffraction pattern of the determined by the cocrystal salt powder diffractometer includes the following lattice plane interval d[A](±0.10 A): 19.06, 7.48, 7.13, 5.86, 4.97, 4.45, 4.20, 3.90, 3.80.

The invention also protects the preparation method of the memantine paroxetine cocrystal salt, which includes the following steps:

Step 1: Dissolve memantine and paroxetine in solvent of −10~25° C. successively, and the volume-mass ratio between the solvent and paroxetine is (1~20 mL): 1 g. Then add the sulfuric acid with the concentration of 10%~80% by dropping. Stir and crystalize for 1~24 h. The molar ratio of memantine, paroxetine and sulfuric acid is (0.8~1.2): (0.8~1.2):(0.8~1.2).

Step 2: The solids are pumped and dried at 40~80° C. for 2~12 h to obtain cocrystal salt.

Further, the solvent temperature in step 1 is 0~10° C.

Further, the volume-mass ratio of the solvent to paroxetine in step 1 is (3~10 mL): 1 g.

Further, the solvent is tetrahydrofuran, acetone, dichloromethane, isopropanol, methanol, ethanol, n-butanol, acetonitrile, ether or ethyl acetate.

Further, the sulfuric acid concentration in step 1 is 3040%.

The invention also protects the application of cocrystal salt in the preparation or prevention of diseases or symptoms, such as Alzheimer's disease, OCD and depression.

The invention also protects a pharmaceutical composition comprising the cocrystal salt and at least one medically acceptable additive, which is a diluent, filler, disintegrating agent, flow aid, lubricant, binder, antioxidant, buffer or colorant.

Further, the diseases or symptoms described are Alzheimer's disease, OCD, depression and Parkinson's disease.

The invention also protects a pharmaceutical composition comprising the cocrystal salt, at least one therapeutic drug and at least one medically acceptable additive. The therapeutic agents are donepezil, galantamine or Rivastigmine.

Further, the diseases or symptoms described are Alzheimer's disease, OCD, depression and Parkinson's disease.

The pharmaceutical compositions of the invention can be prepared according to well-known methods, which are suitable for gastrointestinal administration (such as oral or rectal administration) and parenteral administration, and for the administration of mammals (warm blooded animals), including human beings. The compositions include a therapeutic effective amount of combination products or cocrystal salts with multi-target effects. They can be used alone or in combination with at least one pharmaceutically acceptable carrier, (especially for gastrointestinal or parenteral applications). Typical oral preparations include tablet, capsule, syrup, oral liquid granules and suspension. Typical injection preparations include solution and suspension. The pharmaceutically acceptable additives suitable for the invention include, but are not limited to, diluent or filler disintegrator, flux, lubricant, binder, colorant and their combination, provided that they are chemically inert and therefore do not have a negative impact on the combined product or the cocrystal salt with multi-target effect. The amount of each additive in a solid preparation can be varied within the normal scope. The typical pharmaceutically acceptable carriers applicable to the preparation are: sugars, such as lactose, sucrose, mannitol and sorbitol; starches, such as corn starch, cassava starch and potato starch; cellulose and its derivatives, such as sodium hydroxy methylcellulose, ethyl cellulose and methylcellulose; calcium phosphate, such as dicalcium phosphate and tricalcium phosphate; sodium sulfate; calcium sulfate; polyvinyl pyrrolidone; polyvinyl alcohol; stearic acid; stearic acid-base earth metal salt, such as magnesium stearate and calcium stearate; stearic acid; vegetable oils, such as peanut oil, cottonseed oil, sesame oil, olive oil and corn oil; nonionic, cationic and anionic surfactants; glycol polymer; β-cyclodextrin; fatty alcohols; and hydrolytic solids of grains and other non-toxic fillers, adhesives, disintegrators, buffers, preservatives, antioxidants, lubricants, colorants and other auxiliary materials commonly used in pharmaceutical preparations Pharmaceutical preparations for gastrointestinal or parenteral administration are, for example, unit dosage forms, such as coated tablets, tablets, capsules, suppositories and ampoules. They can be prepared according to well-known methods, such as traditional mixing, pelletizing, coating, concentrated solution or freeze-drying. Therefore, a pharmaceutical composition for oral use may be obtained by mixing a linked prodrug, a combination product or a cocrystal salt with a solid excipient, granulating the obtained mixture if necessary, and, if necessary, making the mixture or particle into a tablet or core of a coated tablet after the addition of a suitable excipient.

The dosage of the cocrystal salt or the active compound in pharmaceutical composition depends on a number of factors, such as the mode of administration, the species of mammal, age and/or individual circumstances. In animal disease model, the dosage range of oral administration with therapeutic effect is from about 0.1 mg/kg/day to about 100 mg/kg/day, and that of human treatment is from about 0.1 mg/day to about 200 mg/day. The preferred dose of the cocrystal salt or pharmaceutical composition of the invention is the therapeutic effective dose.

Compared with the existing technology, the invention has the following advantages: The cocrystal salt of the invention is memantine paroxetine sulfate. The mechanism of action is 5-HT inhibitor and NMDA receptor antagonist, which is multi-target drug. For patients, in addition to the advantages of its multi-target mechanism, the cocrystal salt can reduce the incidence of complications, reduce the recurrence rate, improve the quality of life of patients, and reduce the burden of home care. In addition to being a multi-target drug, the cocrystal salt of the invention can also form a compound preparation or be used in combination with other drugs with different action mechanisms, so as to obtain an unexpected clinical effect According to the preliminary pharmacokinetic test of memantine paroxetine cocrystal salt and memantine, the cocrystal salt can improve the drug absorption, significantly increase the blood concentration, improve the bioavailability, and provide the material basis for reducing the dosage and adverse drug reactions. By comparing the main pharmacokinetic parameters and their ratios of the same molar dose of memantine paroxetine cocrystal salt and memantine hydrochloride, it can be found that the main pharmacokinetic parameters such as $T_{1/2}$, $T_{max}$, $C_{max}$ and $AUC_{(0-\infty)}$ were significantly difference in the ratios. The results showed that: $T_{1/2}$ time was significantly longer, which was 2.79 times; $T_{max}$ time was longer, which was 1.41 times; $C_{max}$ value was significantly increased, which was 1.62 times; $AUC_{(0-\infty)}$ was significantly strengthened, which was 4.10 times. The results indicate that the cocrystal salt can change the pharmacokinetic parameters of the drug under the same dosage, especially can improve the absorption capacity of memantine in vivo, and can reduce the dosage and the adverse reactions of the drug under the same blood concentration.

Therefore, the cocrystal salt of the invention can produce the corresponding curative effect through the multi-target mechanism. At the same time, after forming the cocrystal salt, it can significantly improve the drug bioavailability of memantine, provide the basis for reducing the drug dosage and adverse reactions, which has important potential clinical application value.

DETAILED DESCRIPTION OF THE EMBODIMENTS

The following is a detailed description of the embodiment of the invention. The embodiment is implemented on the premise of the technical scheme of the invention, and the detailed implementation mode and specific operation process are given. However, the protection scope of the invention is not limited to the following embodiments.

The apparatus for detecting the structure and performance of cocrystal salt in the embodiment of the invention is as follows:

1. X-ray powder diffractometer, RIGAKU TTR III high power X-ray diffractometer of Japanese science company, test conditions: Cu target, 40 kV, 40 mA, 3°-50°, target/filter-Cu/Ni filter, current/voltage-40.0 mA/40.0 kV, 2θ angle range: 3°-50°);

2. Fourier transform infrared spectrometer, Thermo Scientific Instrument Co. U.S.A, Nicolet 8700 Fourier transform infrared spectrometer;

3. Bruker Avance III 400 superconducting nuclear magnetic resonance instrument, determination solvent: DMSO-d, internal standard: TMS;

4. TQ/Orbitrap XL Fourier Fourier transform electrostatic field orbit mass spectrometer of Thermal Power Company.

Embodiment 1 Preparation of $C_{19}H_{20}FNO_3 \cdot C_{12}H_{21}N \: H_2SO_4 \cdot 3H_2O$ Add 120 g (0.282 mol) of paroxetine mesylate into the reaction flask. Add 1200 mL of 1 mol/L sodium hydroxide solution. Add 1200 mL of ethyl acetate. Keep the temperature below 30° C. Stir until it is clear and solid-free. Leave it standing and stratified. Wash the organic phase three times with water. Add anhydrous sodium sulfate to dry for 4 h. Filter and wash. Reduce the pressure to concentrate. Keep the prepared paroxetine for use;

Add 60 g (0.278 mol) of memantine hydrochloride into the reaction flask. Add 200 mL of 1 mol/L sodium hydroxide solution. Add 200 mL of dichloromethane. Keep the temperature below 30° C. Stir it until it is clear and solid-free. Leave it standing and stratified. Wash the organic phase three times with water. Add anhydrous sodium sulfate to dry for 4 h. Filter and wash. Reduce the pressure and concentrate. Keep the prepared memantine for use;

Dissolve 77.4 g (0.2350 mol) of paroxetine with 387 mL of tetrahydrofuran, transfer it to a reaction flask, add 42.1 g (0.235 mol) of memantine, and stir evenly. In an ice water bath, keep the temperature at 0-10° C., stir and add 69.5 g (0.235 mol) of 33% sulfuric acid. Then stir and crystalize at 5° C. for 4 h and filter. Blow the solids at 50° C. for 8 h and get 117.1 g white solids. The yield is 82.1%.

The reaction flow diagram is as follows:

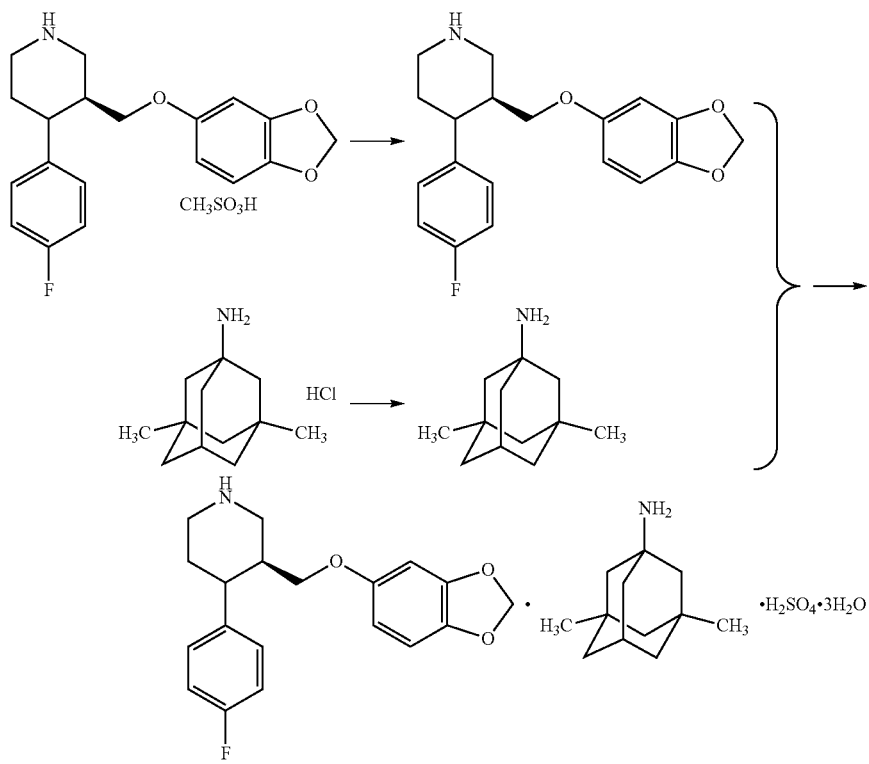

The cocrystal salt of $C_{19}H_{20}FNO_3 \cdot C_{12}H_{21}N \cdot H_2SO_4 \cdot 3H_2O$ prepared in this embodiment has the following structural formula:

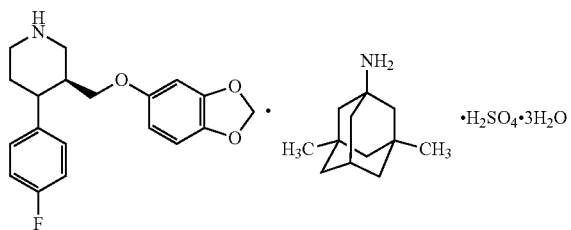

The product prepared in this embodiment is characterized by:

1. X-Ray Powder Diffraction Characterization

Figure 1:
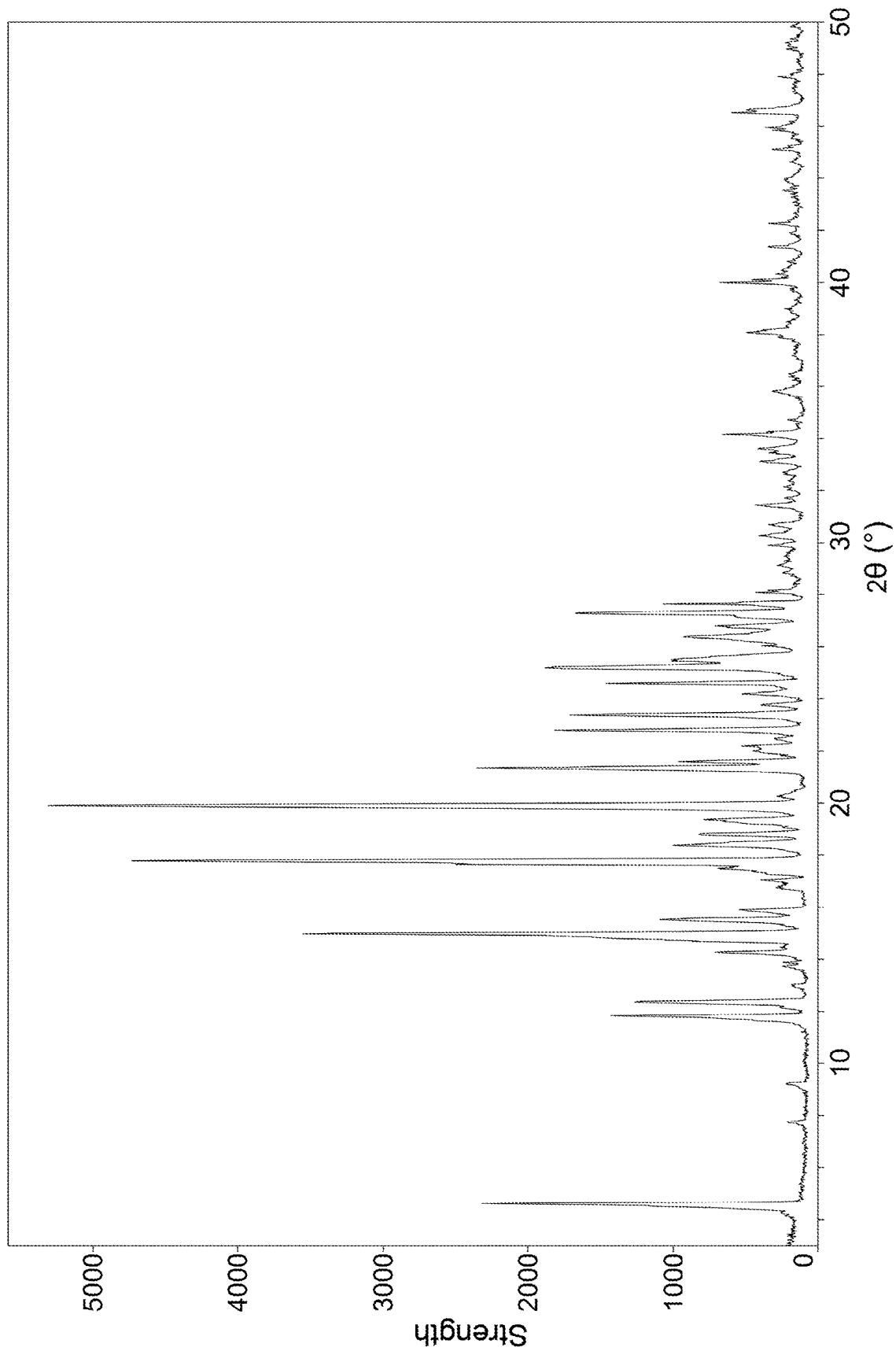
FIG. 1 is the X-ray powder diffraction pattern of $C_{19}H_{20}FNO_3 \cdot C_{12}H_{21}N \cdot H_2SO_4 \cdot 3H_2O$ in embodiment 1 of the invention.

X-ray diffraction analysis is performed on the samples using a Rigaku TTR III high-power X-ray diffractometer from RIGAKU Company. Test conditions: Cu target, 40 kV, 40 mA, 3°-50°, target/filter: Cu/Ni filter, current/voltage: −40.0 mA/40.0 kV, 2θ Angle range: 3°-50°). The measured d(Å) value of X-ray powder diffraction is: 19.0629, 7.4792, 7.1407, 5.9035, 4.9778, 4.4550, 4.1107, 3.8866, 3.7882. The X-ray diffraction pattern is shown in FIG. 1. As shown in FIG. 1, the corresponding 2θ values of the cocrystal salt prepared in this embodiment are 4.6180, 11.8380, 12.3792, 14.9811, 17.7805, 19.8995, 21.6020, 22.80, 23.381.

2. Infrared Spectrum Characterization

Figure 2:
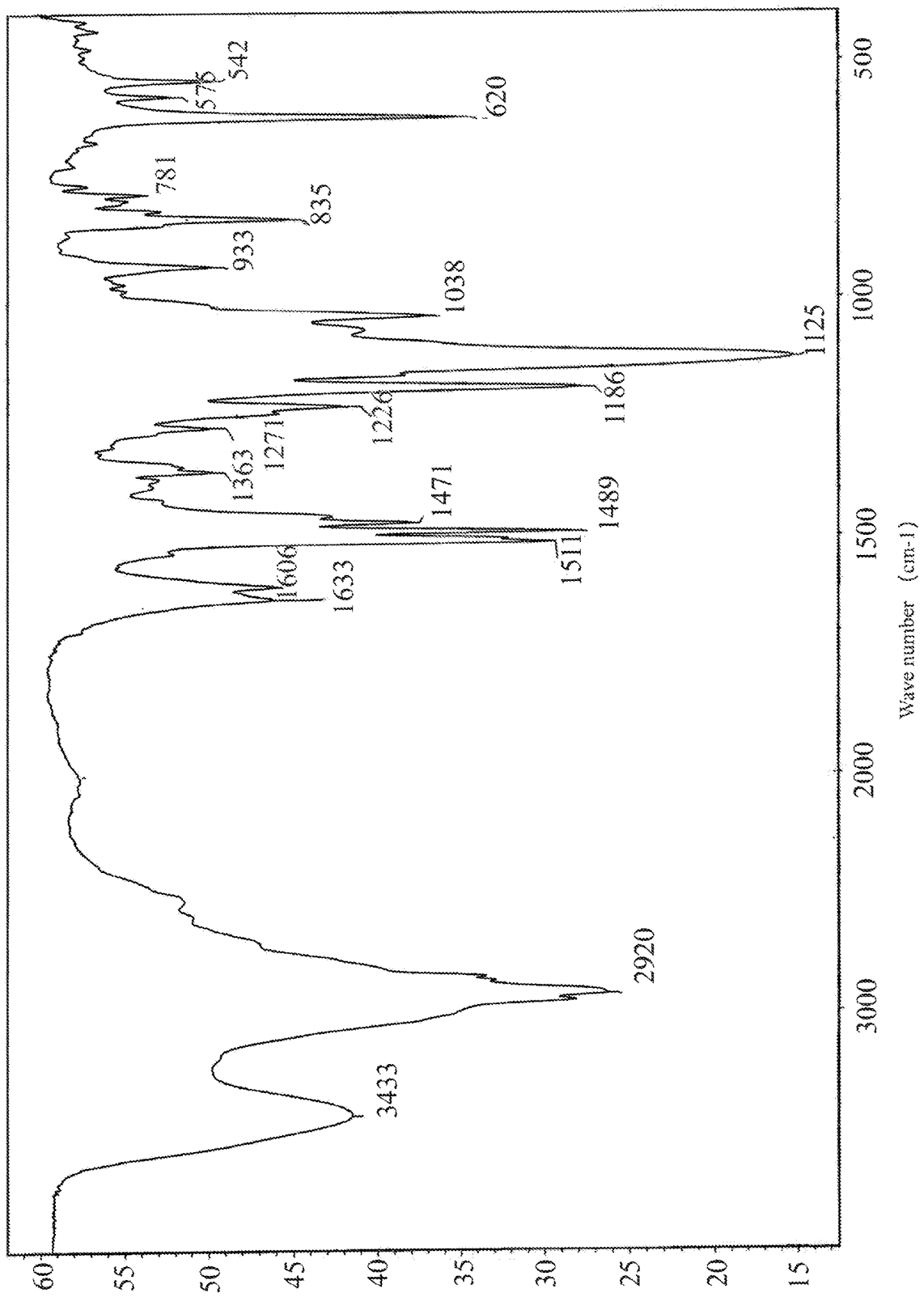
FIG. 2 is the infrared spectrogram of $C_{19}H_{20}FNO_3 \cdot C_{12}H_{21}N \cdot H_2SO_4 \cdot 3H_2O$ in embodiment 1 of the invention.

The cocrystal salt is characterized by infrared absorption spectrum obtained by Fourier transform infrared spectroscopy (FT-IR), using the following important bands (expressed by the reciprocal of wavelength data ($cm^{-1}$)): Nicolet 8700 FT-IR spectrometer of Thermo Scientific Instrument Co. U.S.A. Test samples are made by KBr tablet. The main absorption peak positions ($cm^{-1}$): 3433 (s), 2920 (s), 1633 (m), 1606 (m), 1511 (m), 1489 (m), 1471 (m), 1226 (m), 1186 (m), 1125 (m), 1038 (m), 933 (m), 835 (m), 620 (m). The infrared spectrum is shown in FIG. 2.

3. NMR Characterization

The sample is tested by Bruker Avance III 400 superconductive nuclear magnetic resonance instrument. The solvent to be tested: DMSO-d. The internal standard: TMS.

Figure 3:
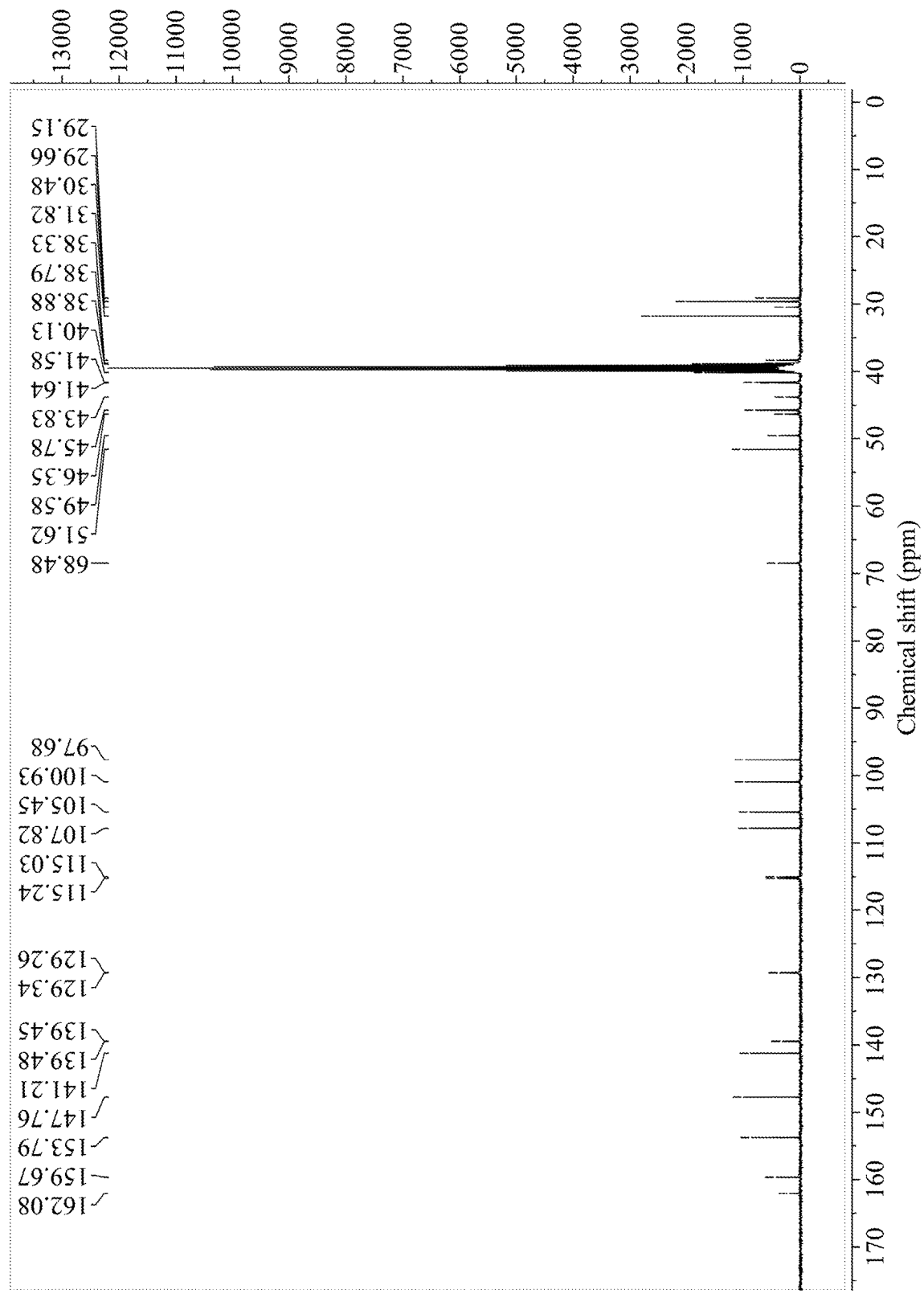
FIG. 3 is the nuclear magnetic resonance carbon spectroscopy of $C_{19}H_{20}FNO_3 \cdot C_{12}H_{21}N \cdot H_2SO_4 \cdot 3H_2O$ in embodiment 1 of the invention.

The $^{13}C$ NMR data (ppm): 162.08, 159.68, 153.79, 147.76, 141.21, 139.48, 129.34, 129.26, 115.24, 115.03, 107.82, 105.45, 100.93, 97.68, 68.48, 51.62, 49.58, 46.35, 45.78, 4 3.83, 41.64, 41.58, 38.79, 38.33, 31.82, 30.48, 29.66, 29.15. The pattern is shown in FIG. 3.

Figure 4:
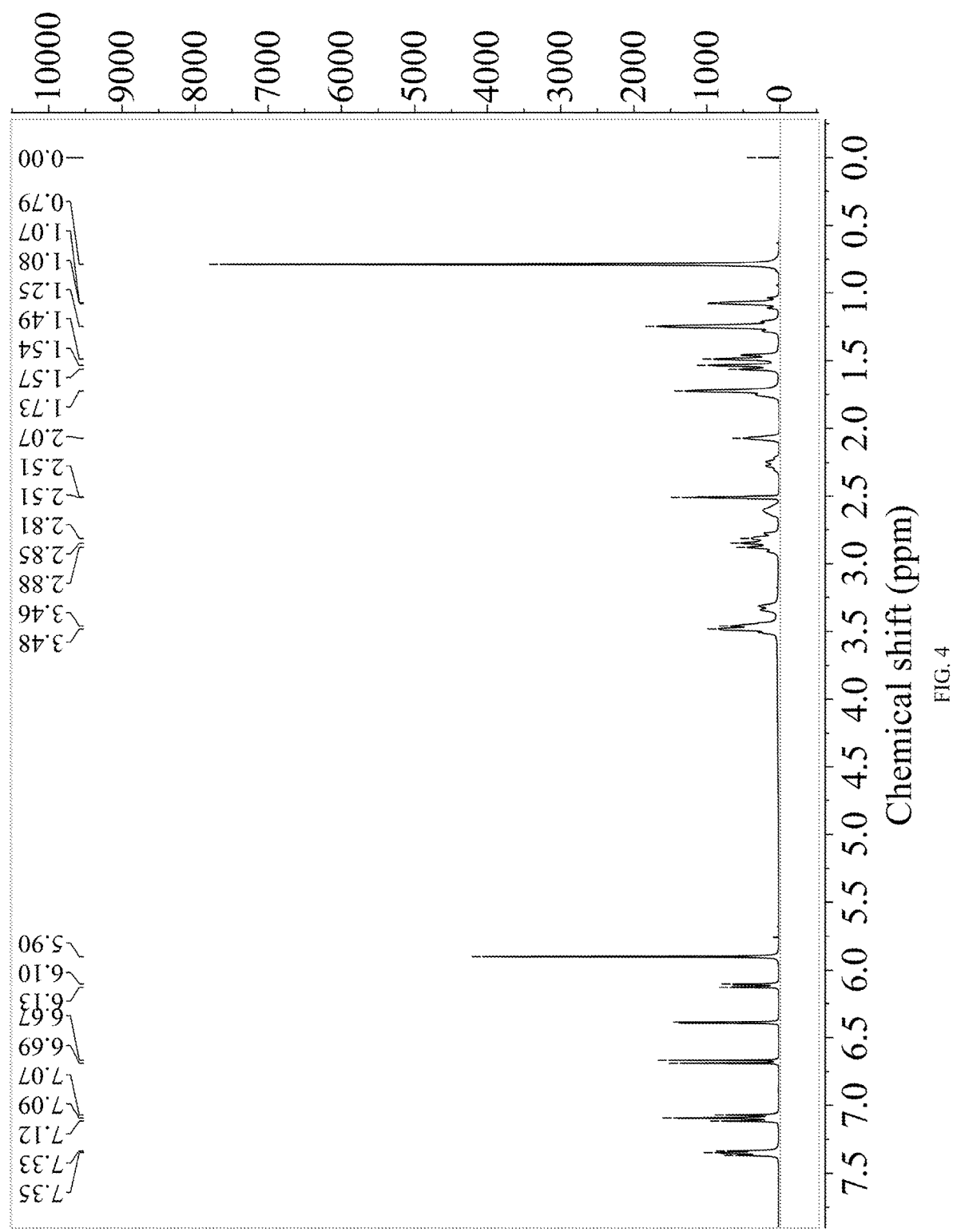
FIG. 4 is the nuclear magnetic resonance hydrogen spectrum of $C_{19}H_{20}FNO_3 \cdot C_{12}H_{21}N \cdot H_2SO_4 \cdot 3H_2O$ in embodiment 1 of the invention.

The $^1H$ NMR data are as follows: 8.32 (Brs, 1H), 7.34 (dd, 2H), 7.08 (t, 2H), 6.67 (d, 1H), 6.38 (d, H), 6.11 (dd, 1H), 5.89 (s, 2H), 4.04 (Brs, 2H), 3.57-3.39 (m, 3H), 3.32 (d, 1H), 2.82 (dt, 3H), 2.60 (s, 1H), 2.25 (d, 1H), 2.06 (s, 1H), 1.73 (m, 3H), 1.50 (dd, 4H), 1.33-1.16 (m, 4H), 1.13-1.00 (m, 2H), 0.78 (s, 6H). The pattern is shown in FIG. 4.

In order to further explain the structural features of the memantine paroxetine cocrystal salt of the invention, 1 g white solid cocrystal salt is taken, dissolved with 100 mL dichloromethane, placed at room temperature for slow crystallization, separated and filtered to obtain transparent block crystal. The block crystal is characterized by single crystal structure test, X-ray powder diffraction, infrared, nuclear magnetic resonance and mass spectrometry, and the characterization results are as follows:

1. Single Crystal Structure Test

Test conditions: single crystal data single crystal X-ray diffractometer, light source: Cu Ka (λ=1.54184 Å); temperature: room temperature; θ angle collection range: 3.60~69.44°

Figure 5:
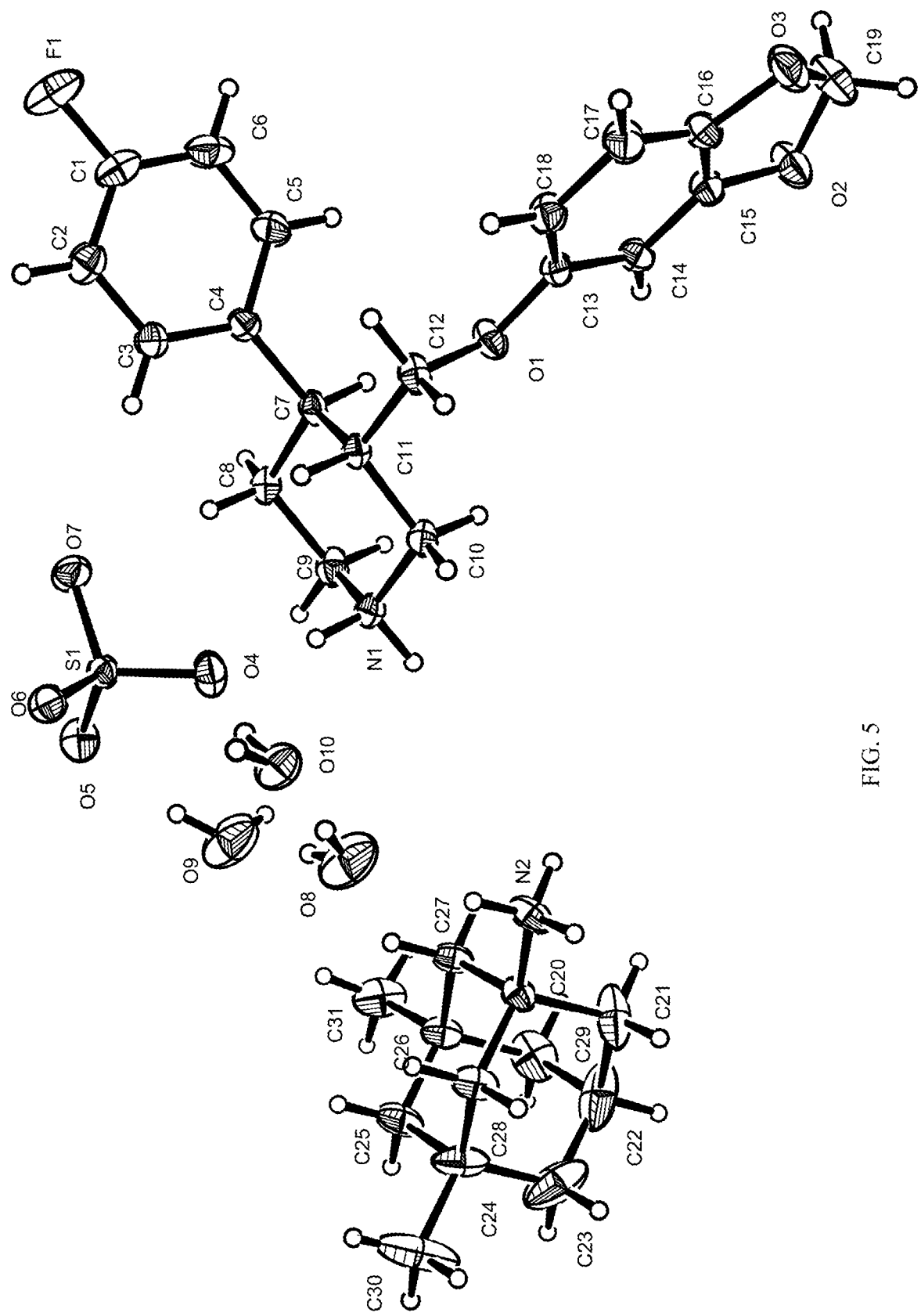
FIG. 5 is the stereogram of $C_{19}H_{20}FNO_3 \cdot C_{12}H_{21}N \cdot H_2SO_4 \cdot 3H_2O$ monocrystal in embodiment 1 of the invention.

Data and Parameters:
Molecular formula: Each unit of molecular formula: $C_{19}H_{21}FNO_3$, $C_{12}H_{22}N$, $O_4S$, $3(H_2O)$; Total molecular formula: $C_{31}H_{49}FN_2O_{10}S$
 Molecular weight: 660.78
 Crystal color: colorless
 Crystal shape: blocky crystal
 Crystal system: orthorhombic system
 Space group: P212121
 Unit cell parameter: A=7.2618(1)
 b=11.9317(1)
 c=38.3731(4)
 alpha=90
 beta=90
 gamma=90
 Z (number of asymmetric units in unit cell): 4
 Calculated strength: 1.320 g/cm$^3$
 According to the crystal composition and molecular formula provided by the entrusting party, $C_{31}H_{49}FN_2O_{10}S$, on the basis of the measured single crystal diffraction data, the possible spatial structure of the crystal obtained through analysis and refinement by WinGX(v1.80.05) software is shown in FIG. 5.

2. X-Ray Powder Diffraction Characterization

The samples are analyzed by RIGAKU TTR III high power X-ray diffractometer of RIGAKU Company. Test conditions: Cu target, 40 kV, 40 mA, 3°-50°, target/filter: Cu/Ni filter, current/voltage: −40.0 mA/40.0 kV, 2θ angle range: 3°-50°). The measured X-ray powder diffraction data d(Å) value: 19.050, 7.461, 7.147, 5.9091, 4.9849, 4.4568, 4.1587, 3.8983, 3.8052.

3. Infrared Spectral Characterization

The cocrystal is characterized by the infrared absorption spectrum obtained by Fourier transform infrared spectroscopy (FT-IR) spectrometer, and the important bands (expressed as the reciprocal of wavelength data (cm$^{-1}$)) described below: Thermo Scientific Instrument Co. U.S.A., Nicolet 8700 Fourier transform infrared spectrometer is used to test the samples prepared by KBr tablet. The main absorption peak positions (cm$^{-1}$): 3432 (s), 2920 (s), 1633 (m), 1606 (m), 1510 (m), 1489 (m), 1471 (m), 1186 (m), 1125 (m), 1038 (m), 933 (m), 620 (m). Compared with the infrared absorption spectra of physical mixtures, the absorption peaks and shifts are very obvious.

4. NMR Spectrum Characterization

The samples are tested by Bruker Avance III 400 superconductive nuclear magnetic resonance. The solvent: DMSO-d. The internal standard: TMS.

The $^{13}C$ nuclear magnetic resonance (NMR) spectral data (PPM): 160.93, 153.79, 147.77, 141.24, 139.38, 129.36, 115.26, 115.06, 107.80, 105.44, 100.96, 97.68, 68.41, 51.69, 49.61, 46.05, 45.67, 43.65, 41.60, 41.42, 38.50, 38.23, 31.82, 30.06, 29.68, 29.18.

The $^1H$ NMR spectrum data are as follows: 8.35 (Brs, 1H), 7.35 (dd, 2H), 7.09 (t, 2H), 6.68 (d, 1H), 6.39 (d, 1H), 6.12 (dd, 1H), 5.90 (s, 2H), 4.06 (Brs, 2H), 3.58-3.40 (m, 3H), 3.33 (d, 1H), 2.83 (dt, 3H), 2.61 (s, 1H), 2.26 (d, 1H), 2.07 (s, 1H), 1.74 (m, 3H), 1.51 (dd, 4H), 1.34-1.17 (m, 4H), 1.14-1.01 (m, 2H), 0.79 (s, 6H).

5. Mass Spectrometry Characterization

Thermo Scientific Instrument Co. U.S.A. TQ/Orbitrap XL Fourier transform electrostatic field orbital trap mass spectrometer is used. Test method: GB/T 6041-2002 general principles of mass spectrometry analysis method. See Table 1 for test results.

TABLE 1

Position and relative abundance of the major fragmentation peaks in the sample quality spectra

| Mass charge ratio (M/Z) (measured value) | Mass charge ratio (M/Z) (theoretical value) | Relative abundance (%) | Molecular formula |
| --- | --- | --- | --- |
| 180.17444 | 180.17468 | 100.00 | $C_{12}H_{22}N_4$ |
| 330.15002 | 330.15000 | 10.19 | $C_{19}H_{21}O_3NF$ |

From the above characterization data, it can be seen that the $C_{19}H_{20}FNO_3 \cdot C_{12}H_{21}N \cdot H_2SO_4 \cdot 3H_2O$ prepared in this embodiment has the same phase and structure as the single crystal, and is quite different from the phase and structure of the mixture obtained by mixing the two active ingredients of memantine and paroxetine through simple materials.

Embodiment 2 Prepares $C_{19}H_{20}FNO_3 \cdot C_{12}H_{21}N \cdot H_2SO_4 \cdot 3H_2O$ Paroxetine and memantine is prepared by taking 50 g paroxetine mesylate and 30 g memantine hydrochloride respectively.

15.98 g (0.0485 mol) paroxetine is added to 80 mL tetrahydrofuran, which is evenly dissolved by stirring; 8.70 g (0.0485 mol) memantine is added and evenly stirred; The solution temperature is maintained at 0-10° C., and 14.4 g of 33% sulfuric acid (0.0485 mol) is added into the solution. After the solution is added, stir and crystalize for 2 h, filter, and the resulting solid is dried at 50° C. for 6 h by air blast, and 21.2 g of white solid is obtained.

NMR data is: $^1$HNMR (400 MHZ, DMSO-d): 7.37 (2H), 7.13 (2H), 6.70 (1H), 6.42 (1H), 6.14 (1H, 5.93 (2H), 3.54-3.46 (3H), 3.33 (1H), 2.86 (3H), 2.26 (1H), 2.10 (1H), 1.75 (3H), 1.56 (4H), 1.28 (4H), 1.14-1.07 (2H), 0.82 (6H); The X-ray powder diffraction characteristic d(Å) value of the prepared white solid: 19.0648, 7.4908, 7.1171, 5.8144, 4.9614, 4.4404, 4.2498, 3.9010, 3.7913.

Embodiment 3 Prepares $C_{19}H_{20}FNO_3 \cdot C_{12}H_{21}N$ $H_2SO_4 \cdot 3H_2O$ Paroxetine and memantine are prepared by taking 50 g paroxetine mesylate and 30 g memantine hydrochloride respectively;

12.35 g (0.0375 mol) paroxetine is added to 62 mL acetone, stirred and dissolved evenly. 6.72 g (0.0375 mol) memantine is added and stirred evenly; The solution temperature is maintained at 0~10° C., and 33% sulfuric acid of 11.13 g (0.0375 mol) is added into the solution. After the solution is added, stir and crystalize for 2 h and filter. The resulting solid is dried at 50° C. by blast air for 6 h, and 10.34 g of white solid is obtained.

The powder X-ray diffraction of the memantine paroxetine cocrystal salt obtained in embodiment 3 has the same characteristic value as the cocrystal salt in embodiment 1.

The HNMR of the memantine paroxetine cocrystal salt obtained in embodiment 3 has the same absorption peak as that in embodiment 1.

Embodiment 4 Prepares $C_{19}H_{20}FNO_3 \cdot C_{12}H_{21}N$ $H_2SO_4 \cdot 3H_2O$ Take 50 g of paroxetine mesylate and 30 g of memantine hydrochloride respectively, and prepare paroxetine and memantine according to the method of embodiment 1;

Add 9.80 g (0.0298 mol) of paroxetine to 49 mL of dichloromethane, stir and dissolve evenly, add 5.34 g (0.0298 mol) of memantine, stir evenly; keep the solution temperature at 0-10° C., add 8.85 g (0.0298 mol) of 33% sulfuric acid into the solution, stir and crystallize for 2 h, filter, dry the solid at 50° C. for 6 h by blast, and obtain 6.38 g of white solid.

The powder X-ray diffraction of the memantine paroxetine cocrystal salt obtained in embodiment 4 has the same characteristic value as that in embodiment 1.

The HNMR of the memantine paroxetine cocrystal salt obtained in embodiment 4 has the same absorption peak as that in embodiment 1.

Embodiment 5 Prepares
$C_{19}H_{20}FNO_3·C_{12}H_{21}N·H_2SO_4·3H_2O$

Take 50 g of paroxetine mesylate and 30 g of memantine hydrochloride respectively, and prepare paroxetine and memantine according to the method of embodiment 1;

Add 11.25 g (0.0342 mol) of paroxetine to 57 mL of isopropanol, stir and dissolve evenly, add 6.13 g (0.0342 mol) of memantine, stir evenly; keep the solution temperature at 0~10° C., add 10.16 g (0.0342 mol) of 33% sulfuric acid to the solution, stir and crystallize for 2 h, filter, and dry the solid at 50° C. by blast for 6 h to obtain 9.74 g of white solid.

The powder X-ray diffraction of the memantine paroxetine cocrystal salt obtained in embodiment 5 has the same characteristic d(Å) value as that in embodiment 1.

The hydrogen NMR of the memantine paroxetine cocrystal salt obtained in embodiment 5 has the same absorption peak as that in embodiment 1.

Embodiment 6: Pharmacokinetic Experiment of Memantine Paroxetine Cocrystal Salt

1. Experimental objective

Determination of the pharmacokinetic parameters of amantadine and paroxetine in rat plasma by LC-MS/MS method 2. Experimental Material 2.1 Main Reagents The memantine paroxetine cocrystal salt prepared in embodiment 1; memantine hydrochloride; dexamethasone (Intermediate inspection office); ammonium formate; methanol is all chromatographic pure (Merck Company); formic acid is all chromatographic pure (Aladdin Company); acetonitrile is all chromatographic pure (Merck Company); experimental water is deionized purified water.

2.2 Animal

SD rat, SPF grade, male, weight 200-250 g, purchased from Zhejiang Experimental Animal Center, production license No.: SCXK (Zhejiang) 2014-0001.

3. Instrument and Equipment

Liquid mass spectrometer: Thermo Finnigan TSQ Quantum, composed of Surveyor As, Surveyor MS Pump Plus and TSQ Quantum, Thermo Fisher Scientific Company; Sartorius BP-211D electronic balance; Thermo STRATOS high speed freezing centrifuge; Eppendorf PCB-11 micro vortex mixer; Milli-Q Grandient pure water meter.

4. Chromatography-Mass Spectrometry Conditions 4.1 Chromatographic Conditions:

Chromatographic column: Waters Cortecs C18 (2.1 mm×50 mm, 2.7 μm); column temperature: 35° C.; mobile phase: acetonitrile-10 mm ammonium formate containing 0.1% formic acid (10:90); flow rate: 0.2 mL·min$^{-1}$; sample injection volume: 5 μL.

4.2 Mass Spectrum Conditions:

Ion detection method: multiple reaction monitoring (MRM); ionic polarity: positive ion (Positive); ionization mode: electrospray ionization (ESI); ionization voltage (IS): 3000.0V; temperature: 300° C.; sheath gas: 35; auxiliary gas: 30. See Table 2 for test results.

TABLE 2

| Detection object | Detection ion | CE(eV) |
|---|---|---|
| Memantine hydrochloride | 180.2→163.0 | 15 |
| Internal standard (dexamethasone) | 393.2→355.2 | 11 |

5. Collection of Rat Blood Samples 10 rats are randomly divided into 2 groups, 5 rats in each group: group A: 5.6 mg/kg memantine hydrochloride; group B: 17.4 mg/kg cocrystal salt;

The rats are fasted for 12 h before the experiment, and the tested drugs re given by gavage with the volume of 1 mL/100 g. Before and 5, 10, 20, 40, 60, 120, 180, 240, 360 and 480 min after administration, 0.5 mL of blood is collected through the fundus vein plexus. Anticoagulate the heparin. Centrifugate at 4000 rpm for 10 min, and separate the plasma. It can be used for the determination of memantine concentration.

TABLE 3

Estimated memantine and cocrystal salt and pharmacokinetic parameters after administration in rats

| Group | Parameter | Unit | Average value | Standard deviation |
|---|---|---|---|---|
| Group A | AUC$_{(0-t)}$ | ng/L * h | 713.726 | 109.856 |
| Group B | | | 1982.124 | 155.293 |
| Group A | AUC$_{(0-\infty)}$ | ng/L * h | 773.35 | 113.602 |
| Group B | | | 3167.23 | 637.631 |
| Group A | MRT$_{(0-t)}$ | h | 2.429 | 0.267 |
| Group B | | | 3.298 | 0.126 |
| Group A | MRT$_{(0-\infty)}$ | h | 3.054 | 0.328 |
| Group B | | | 8.1 | 2.474 |
| Group A | T$_{1/2}$z | h | 2.009 | 0.268 |
| Group B | | | 5.605 | 1.861 |
| Group A | T$_{max}$ | h | 0.617 | 0.407 |
| Group B | | | 0.868 | 0.181 |
| Group A | CLz/F | L/h/kg | 7406.228 | 1188.233 |
| Group B | | | 5664.876 | 1071.185 |
| Group A | Vz/F | L/kg | 21319.791 | 3196.406 |
| Group B | | | 43816.086 | 8037.842 |
| Group A | C$_{max}$ | ng/L | 276.249 | 56.868 |
| Group B | | | 449.186 | 34.668 |

7. Result and Discussion

By comparing the main pharmacokinetic parameters and their ratios of the same molar dose of memantine paroxetine cocrystal salt and memantine hydrochloride, it can be found that the main pharmacokinetic parameters such as T$_{1/2}$, T$_{max}$, C$_{max}$ and AUC$_{(0-\infty)}$ were significantly different; The results show that: T$_{1/2}$ time is significantly longer, which is 2.79 times; T$_{max}$ time is longer, which is 1.41 times; C$_{max}$ value is significantly increased, which is 1.62 times; AUC$_{(0-\infty)}$ is significantly strengthened, which is 4.10 times.

The above is only a better embodiment of the invention and does not limit the invention. Any modification, equivalent replacement and improvement made within the spirit and principles of the invention shall be included in the protection scope of the invention.

What is claimed is:

1. A memantine paroxetine cocrystal salt, wherein a molecular formula of the memantine paroxetine cocrystal salt is $C_{19}H_{20}FNO_3 \cdot C_{12}H_{21}N \cdot H_2SO_4 \cdot XH_2O$, wherein X is 3, and a memantine molecule and a paroxetine molecule are bound by a non-covalent bond, wherein the memantine paroxetine cocrystal salt comprises following lattice plane intervals d[A](±0.10 A): 19.06, 7.48, 7.13, 5.86, 4.97, 4.45, 4.20, 3.90, 3.80 determined by an X-ray powder diffractometer.

2. A preparative method for the memantine paroxetine cocrystal salt according to claim 1, comprising the following steps:
   step 1: dissolving a memantine and a paroxetine in a −10-25° C. solvent successively to obtain a dissolved solution, wherein a volume-mass ratio between the solvent and the paroxetine is (1-20 mL):1 g, then dropwise adding sulfuric acid with a concentration of 10%-80% to the dissolved solution to obtain a mixed solution, then stirring and crystallizing the mixed solution for 1-24 h to obtain a crystalline solid, wherein a molar ratio of the memantine, the paroxetine and the sulfuric acid of the crystalline solid is (0.8-1.2):(0.8-1.2):(0.8-1.2),
   step 2: filtering the crystalline solid and drying the crystalline solid at 40-80° C. for 2-12 h to obtain the memantine paroxetine cocrystal salt.

3. The preparative method for the memantine paroxetine cocrystal salt according to claim 2, wherein the temperature of the solvent in step 1 is 0-10° C.

4. The preparative method for the memantine paroxetine cocrystal salt according to claim 2, wherein the volume-mass ratio of the solvent to the paroxetine is (3-10 mL):1 g in step 1.

5. The preparative method for the memantine paroxetine cocrystal salt according to claim 2, wherein the solvent is one selected from the group consisting of tetrahydrofuran, acetone, dichloromethane, isopropanol, methanol, ethanol, n-butanol, acetonitrile, ether and ethyl acetate.

6. The preparative method for the memantine paroxetine cocrystal salt according to claim 2, wherein the concentration of the sulfuric acid is 30-40% in step 1.

7. A pharmaceutical composition, comprising the memantine paroxetine cocrystal salt according to claim 1, and at least one pharmaceutically acceptable additive, wherein the pharmaceutically acceptable additive is one selected from the group consisting of diluents, fillers, disintegrating agents, flow aids, lubricants, adhesives, antioxidants, buffers and colorants.

8. The pharmaceutical composition according to claim 7, further comprising at least one therapeutic agent wherein the therapeutic agent is one selected from the group consisting of donepezil, galantamine and Rivastigmine.

9. The preparative method for the memantine paroxetine cocrystal salt according to claim 3, wherein the solvent is one selected from the group consisting of tetrahydrofuran, acetone, dichloromethane, isopropanol, methanol, ethanol, n-butanol, acetonitrile, ether and ethyl acetate.

10. The preparative method for the memantine paroxetine cocrystal salt according to claim 4, wherein the solvent is one selected from the group consisting of tetrahydrofuran, acetone, dichloromethane, isopropanol, methanol, ethanol, n-butanol, acetonitrile, ether and ethyl acetate.

* * * * *